(12) United States Patent
Taylor et al.

(10) Patent No.: US 8,028,395 B2
(45) Date of Patent: Oct. 4, 2011

(54) METHOD FOR MANUFACTURING HIGH FLOW INSUFFLATION NEEDLE STYLET

(75) Inventors: Scott V. Taylor, Mission Viejo, CA (US); Paul Balschweit, Mission Viejo, CA (US); Matthew A. Wixey, Dana Point, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 1030 days.

(21) Appl. No.: 11/868,901

(22) Filed: Oct. 8, 2007

(65) Prior Publication Data

US 2008/0083257 A1 Apr. 10, 2008

Related U.S. Application Data

(60) Provisional application No. 60/828,573, filed on Oct. 6, 2006.

(51) Int. Cl.
*B23P 13/04* (2006.01)
*B21C 37/06* (2006.01)

(52) U.S. Cl. ............................................. 29/557; 72/368

(58) Field of Classification Search .................... 29/557; 72/368, 370.27; 604/272, 158, 23, 264; 606/185
See application file for complete search history.

(56) References Cited

U.S. PATENT DOCUMENTS

| | | |
|---|---|---|
| 6,202,465 B1 | 3/2001 | Jankoski et al. |
| 6,656,160 B1 | 12/2003 | Johnson et al. |
| 2003/0116543 A1 | 6/2003 | Battaglia |

OTHER PUBLICATIONS

Co-Pending U.S. Appl. No. 11/009,440, filed Dec. 9, 2004. Title: Insufflation Gas Warmer and Humidifier.
Co-Pending U.S. Appl. No. 11/680,835, filed Mar. 1, 2007 Title: Gas Insufflation and Suction/Irrigation Tubing.
Co-Pending U.S. Appl. No. 11/062,022, filed Feb. 18, 2005. Title: Surgical Access Apparatus and Method.
Co-Pending U.S. Appl. No. 11/383,927, filed May 17, 2006. Title: Surgical Access Apparatus and Method.
The International Bureau of WIPO, International Preliminary Report on Patentability for International Application No. PCT/US2007/80731 dated Apr. 7, 2009, entitled "Method for Manufacturing High Flow Insufflation Needle Stylet".
International Searching Authority, International Search Report and the Written Opinion of the International Searching Authority for International Application No. PCT/US2007/80731 mailed Jul. 21, 2008.

*Primary Examiner* — John C Hong
(74) *Attorney, Agent, or Firm* — Rimas T. Lukas; John F. Heal; David G. Majdali

(57) ABSTRACT

A method for forming a high flow insufflation needle stylet having distal, intermediate and proximal sections includes providing a flat sheet of metal and forming pilot holes in the sheet proximate opposed edges of the sheet. A profile of a flat pattern of the stylet is formed. The flat pattern has a proximal end, a distal end and a pair of substantially longitudinal edges. At least one support tab is positioned between the flat pattern and the sheet. The intermediate and the proximal sections of the stylet are progressively formed into a partial cylindrical shape with the proximal end being open and the longitudinal edges in the intermediate and proximal sections being positioned between about 90° and 180° apart. The distal section is progressively formed into a substantially cylindrical shape having a closed distal end. The stylet is trimmed from the sheet by cutting the at least one support tab.

18 Claims, 6 Drawing Sheets

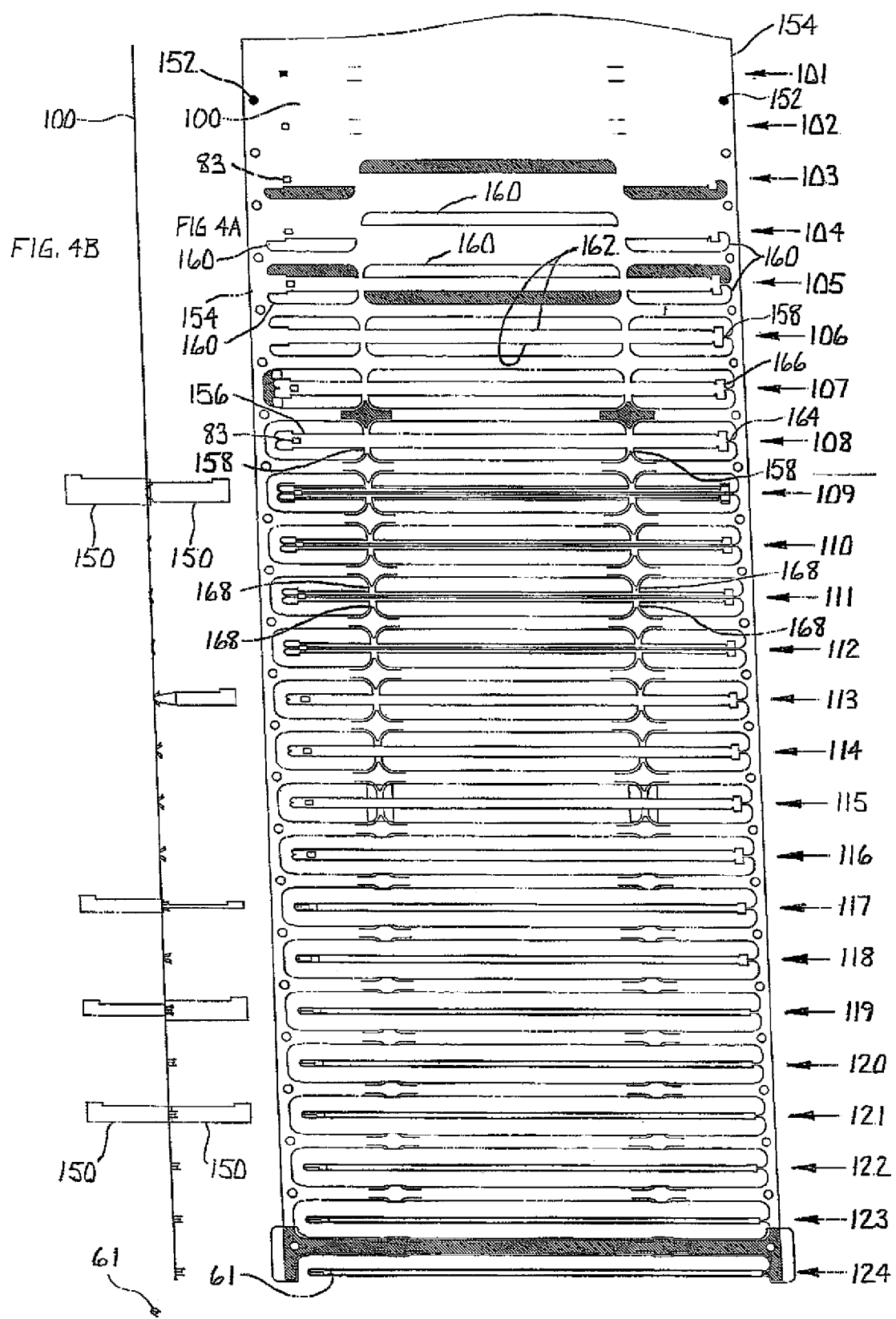

METHOD FOR MANUFACTURING HIGH FLOW INSUFFLATION NEEDLE STYLET

CROSS-REFERENCE TO RELATED APPLICATIONS

This application claims the benefit of U.S. Provisional Patent Application No 60/828,573, filed Oct. 6, 2006, the entire disclosure of which is hereby incorporated by reference as if set forth in full herein.

BACKGROUND

The advantages of less invasive methods of abdominal surgery have been well documented. Reduced infection rates, decreased patient trauma and faster healing times have all been associated with the use of laparoscopic procedures, in which small surgical instruments are introduced into the abdominal cavity through the working channel of a trocar or other access device inserted through the abdominal wall muscle.

During these procedures, the abdominal cavity remains essentially a closed system. In order to improve visibility and increase working space for surgeons, it is preferable to distend the abdominal wall. This is usually accomplished through gas insufflation, in which carbon dioxide or another gas is introduced into the abdominal cavity to distend the abdominal wall and increase the volume of the abdominal cavity Insufflation is typically accomplished using needle assemblies having a hollow cylindrical configuration. A needle having a sharpened distal tip is forced through the abdominal wall to provide access to the abdominal cavity through an insufflation channel. Once the sharpened tip is within the abdominal cavity, care must be taken to avoid puncturing internal organs. For this reason an obturator or stylet has been provided with the insufflation needle. As soon as the needle penetrates the abdominal wall, a blunt tip of the obturator moves beyond the sharpened tip of the needle to inhibit the further penetration of tissue.

During the insufflation process, it is desirable to maximize the flow of gases into the abdominal cavity to reduce the inflation time. Often, a patient will require as much as three liters of insufflation gas. With a typical insufflation flow rate of 600 milliliters per minute, this volume will require five minutes to fully insufflate the cavity. Even a slight reduction in the period of insufflation could significantly reduce operational procedure time and therefore result in a significant cost savings to the hospital and patient.

It is also important to ensure rapid protection of internal organs from the sharp needle tip following penetration of the abdominal wall. Typically, insufflation needle stylets or obturators are biased from a proximal position, wherein the sharpened tip is unprotected to facilitate penetration of the abdominal wall, to a distal position where the sharpened tip is isolated to prevent damage to the interior organs. A fast transition from the proximal position to the distal position increases the safety of the insufflation needle.

An insufflation needle assembly that promotes both rapid insufflation and fast transition of the obturator to isolate the sharp tip of the needle has been described in U.S. Pat. No. 6,656,160 to Taylor, Johnson and Hilal. In the '160 patent, an insufflation needle apparatus is disclosed in which the obturator is formed from a metal tube that is machined to remove portions of the obturator wall. Removing portions of the obturator wall reduces the mass of the obturator, resulting in a faster transition time and thus better protecting internal organs from inadvertent puncture wounds. Also, removing portions of the obturator wall increases the cross-sectional area of the insufflation channel, resulting in an increased insufflation rate.

The needle assembly of the '160 patent provides benefits in terms of safety and efficiency, but the costs associated with machining the metal obturator portion of the assembly also increases the cost of the assembly. Thus, a method of manufacturing the obturator that is more cost-efficient would result in significant savings to hospitals and patients, while maintaining the safety and efficiency of assemblies having reduced obturator wall portions.

SUMMARY

In accordance with the present invention, the high cost of manufacturing the obturator or stylet has been overcome by manufacturing the stylets by a technique using a thin sheet of metal in a progressive die to stamp and roll the metal into the final configuration.

In one aspect, the invention includes a method for forming a high flow insufflation needle stylet. The method includes providing a flat sheet of metal and forming pilot holes in the sheet of metal that are proximate opposed edges of the sheet of metal. The method also includes forming a strip within the sheet with the strip remaining affixed to the sheet at all times during formation of the stylet by at least one support tab. The strip is in the configuration of a flat pattern of the stylet. The method further includes progressively forming the strip into a stylet having a distal section, an intermediate section and a proximal section that extends proximally of the intermediate section. The distal section is formed into a substantially cylindrical shape having a closed distal end. The intermediate section and the proximal section are formed into a partial cylindrical shape with edges of the strip in the intermediate section and the proximal section being formed to between about 90° and 180° apart. The proximal section has an open proximal end. Additionally, the method includes trimming the stylet from the sheet by cutting the at least one support tab.

The forming a strip step may include forming openings along each side of the strip. The openings correspond with the length of the flat pattern of the stylet. The openings are separated by a distance corresponding to a width of the strip. The profile of the edges along the length of the flat pattern of the stylet is included along the edges of the openings closest to each other. The at least one support tab may include a first support tab positioned between the proximal end of the strip and the sheet of metal and at least one second support tab positioned between each side of the strip and the sheet of metal. The closed distal end of the stylet may be formed into a semispherical shape. The method may also include sequentially forming multiple stylets from the sheet of metal. Additionally, the method may include forming apertures in the strip.

In another aspect, the invention includes a method for forming a high flow insufflation needle stylet having a distal section, an intermediate section and a proximal section that extends proximally of the intermediate section. The method includes providing a flat sheet of metal and forming pilot holes in the sheet of metal proximate opposed edges of the sheet of metal. The method also includes forming a profile of a flat pattern of the stylet within the sheet with at least one support tab positioned between the flat pattern of the stylet and the sheet. The flat pattern has a proximal end, a distal end and a pair of substantially longitudinal edges. The method further includes progressively forming the intermediate section of the stylet and the proximal section of the stylet into a partial cylindrical shape with the proximal end being open and the longitudinal edges in the intermediate section and the proximal section being positioned between about 90° and 180° apart. Additionally, the method includes progressively forming the distal section into a substantially cylindrical shape having a closed distal end and trimming the stylet from the sheet by cutting the at least one support tab.

These and other features and advantages of the invention will become more apparent with a discussion of embodiments in reference to the associated drawings.

BRIEF DESCRIPTION OF THE DRAWINGS

FIG. 4A is a top view drawing showing a metal sheet and a series of steps to produce the stylet of FIGS. 2 and 3;

FIG. 4B is a side view drawing showing the metal sheet and a series of steps to produce the stylet of FIGS. 2 and 3.

DETAILED DESCRIPTION

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the structures and/or methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

Figure 1:
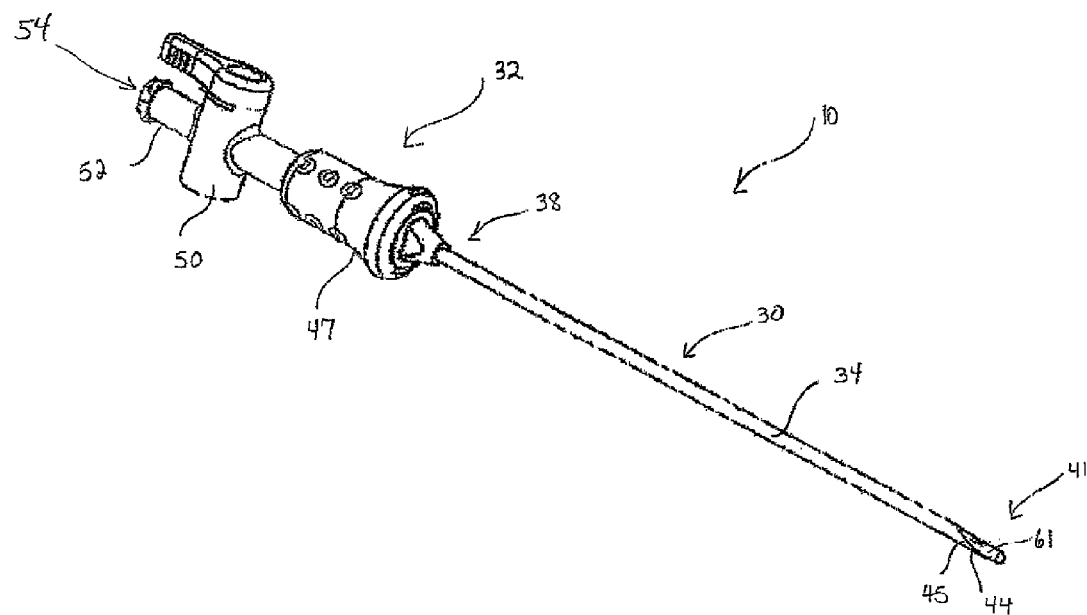
FIG. 1 is a drawing of an insufflation needle apparatus.

An insufflation needle apparatus 10 includes an elongate needle 30 extending distally from a handle 32, as shown in FIG. 1. The needle 30 has a generally hollow cylindrical configuration with a wall 34 extending along an axis between a proximal end 38 and a distal end 41. This wall 34 defines a lumen. A sharpened tip 44 is provided at the distal end 41 of the needle 30, by producing a beveled surface 45.

The proximal end of the needle 30 is fixed to the handle 32 which may include a housing 47, a stopcock or valve 50, and a connector 52 for flexible tubing. Each of these elements defines part of an insufflation channel 54 which extends consecutively from the gas source 18 through the tubing, the connector 52, the valve 50, and the housing 47, into the lumen of the needle 30.

Figure 2:
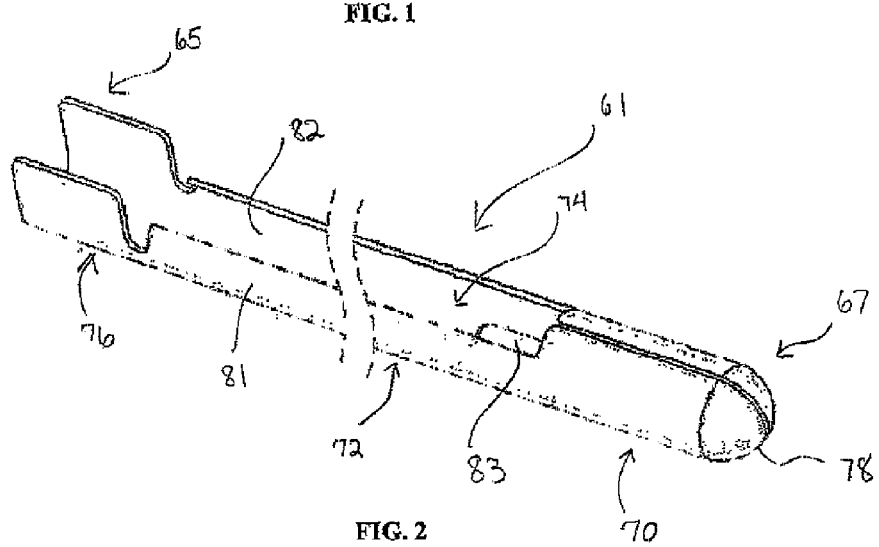
FIG. 2 is a drawing showing the enlarged proximal and distal ends of an obturator or stylet associated with the insufflation apparatus of FIG. 1.

Of particular interest to the needle insufflation apparatus 10 is the importance of having some means for isolating the sharpened tip 44 once the abdominal wall is penetrated, in order to avoid puncturing interior organs. In a preferred embodiment, this feature is associated with an obturator or stylet 61 which is disposed within the lumen of the needle 30. This obturator 61 may have a cylindrical tubular configuration and an axis that extends between a proximal end 65 and a distal end 67, as shown in FIG. 2.

The obturator 61 is formed in the general shape of a tube with a distal section 70, an intermediate section 72 having an outlet port 74, and a proximal section 76 extending proximally of the intermediate section 72. In the distal section 70, the tube is provided with a blunt, nontraumatic distal tip 78. The distal section 70 may include a substantially cylindrical shape having a closed end 78. The blunt, closed end 78 of the distal section 70 may have a semispherical shape. In the intermediate section 72 and proximal section 76, the obturator tube has a generally cylindrical wall 81 defining an interior lumen 82. Portions of the wall 81 are removed to form the outlet port 74 in the intermediate section 72 and proximal section 76. In the illustrated embodiment, a second outlet port 83 is provided in opposing relationship to the port 74. A proximal end of the proximal section 76 is open.

The obturator 61 is moveable axially between a proximal position, wherein the obturator 61 facilitates exposure of the sharpened tip 44, and a distal position (illustrated in FIG. 1) wherein the obturator 61 covers or isolates the sharpened tip 44.

When the needle insufflation apparatus 10 is initially inserted through the abdominal wall, the blunt, nontraumatic tip 78 of the obturator or stylet 61 is moved proximally to expose the sharpened tip 44 of the needle 30. Thus the needle is permitted to penetrate the abdominal wall in order to provide the insufflation channel 54 across the abdominal wall. When the sharpened tip 44 penetrates the abdominal wall, pressure on the blunt distal tip 78 ceases, and the obturator 61, typically spring-biased, moves to its protective distal position as illustrated in FIG. 1.

With the obturator 61 operatively disposed in this distal position, insufflation of the abdominal cavity can begin. In the operative position, the tube is disposed within the lumen of the needle 30, so that insufflation takes place primarily through the lumen 82 of the stylet.

For reasons previously discussed, it is desirable that the insufflation channel 54 be as large as possible to permit rapid inflation of the abdominal cavity. As described in U.S. Pat. No. 6,656,160, this area is dramatically increased by machining the tube used to manufacture the stylet, to remove a portion of the wall 81 along substantially the entire length of the stylet. This provides the cross-section of the wall 81 with a U-shaped configuration along much of its length. The remaining portion of the wall 81 may include apertures, such as second outlet port 83, to further increase the area of the insufflation channel 54 and to reduce the mass of the stylet 61.

In order that the wall 81 of the obturator 61 might be properly centered within the lumen of the needle 30, it is preferable if the circular cross-section of the wall 81 be left with a circumference greater than 180° Preferably this circumference should be in a range between 180° and about 270°, so that between ½ and ¾ of the circular cross-section of the wall 81 remains.

Removing a portion of the wall 81 greatly increases the insufflation gas flow rate through the apparatus 10. The wall 81 has an inner cylindrical surface with a radius $r_1$. Similarly, the wall 34 of the needle 30 has an inner cylindrical surface with a radius $r_2$. Prior to removing a portion of the wall 81, the insufflation channel 54 is restricted to the cross-sectional area of the lumen 82. This area can be computed in accordance with the well known formula for the area of a circle:

$$A = \pi r_1^2 \qquad \text{(Formula 1)}$$

Where, A=cross-section area of the lumen 82 and $r_1$=radius of interior surface of wall 81.

When a portion of the wall 81 is removed, the area of the insufflation channel is increased to a value greater than that computed in accordance with Formula 1. This area can be determined generally in accordance with the following formula:

$$A_s = \pi[r_2^2 - \beta(r_3^2 - r_1^2)] \tag{Formula 2}$$

Where, $A_s$=the cross-sectional area of the insufflation channel; $r_1$=radius of the interior surface of the wall 81; $r_2$=radius of the interior surface of the wall 34; $r_3$=radius of the exterior surface of the wall 81; and $\beta$=the fractional portion of the radial circumference of the wall 81.

It will be noted that the coefficient $\beta$ represents the fractional portion of the radial circumference of the wall 81 which remains after the wall portion is removed. If ½ of the wall 81 remains, the coefficient $\beta$ is equal to ½. When the remaining portion of the wall 81 is greater than 180° in order to facilitate centering of the obturator 61 within the needle 30, the coefficient $\beta$ in Formula 2 may be ⅔, for example.

The mass of the obturator 61 is also reduced in direct proportion to the amount of the wall 81 which is removed. Reducing this mass facilitates the speed with which the obturator can be moved by a spring between its proximal position and its protective distal position.

By removing a portion of the wall 81, the mass of the obturator 61, is significantly reduced. This increases the speed with which the obturator 61 can be moved from its initial proximal position to its safe distal position. This substantially eliminates undesirable organ sticks once the needle 30 penetrates the abdominal wall.

Figure 5A:
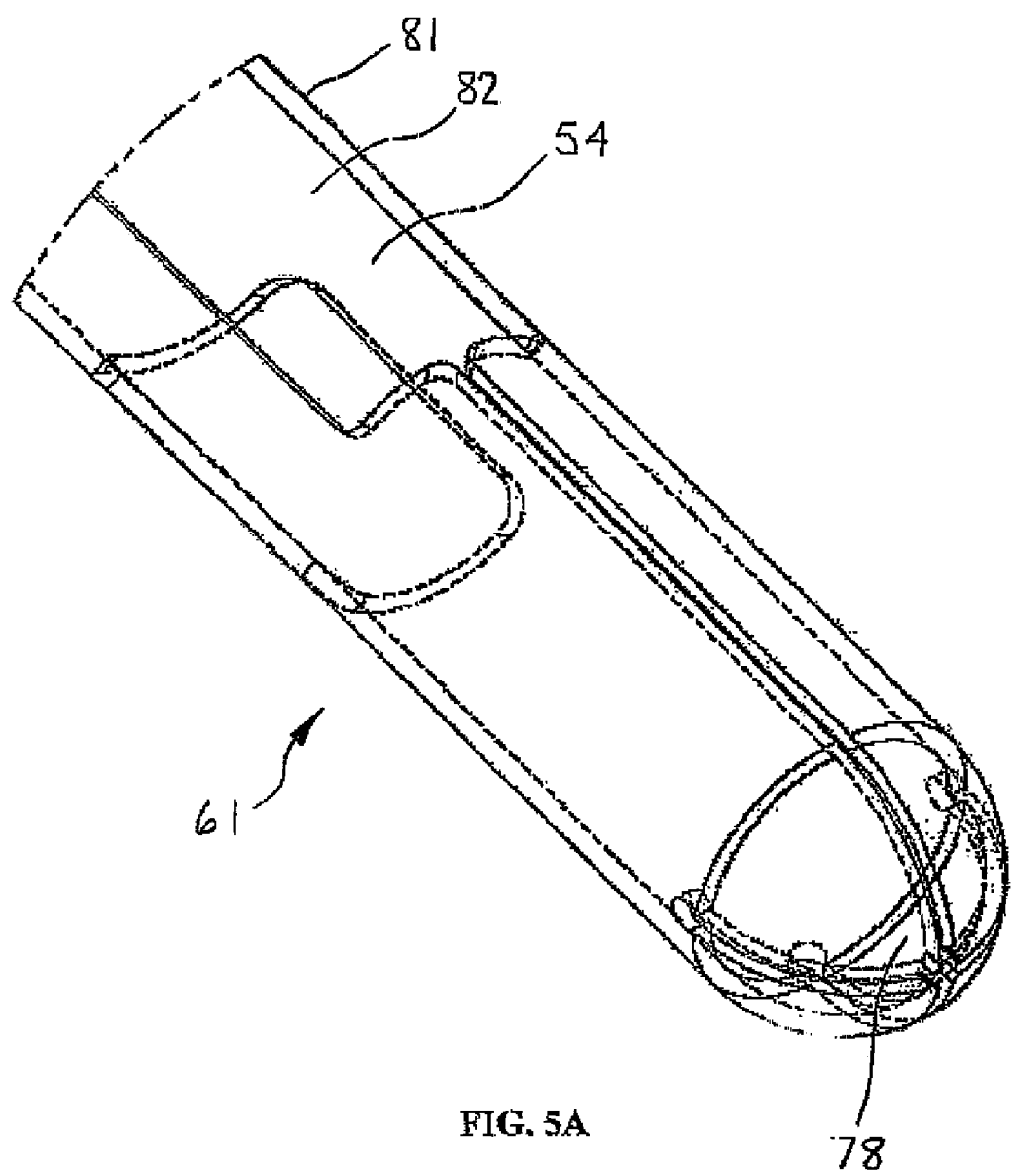
FIGS. 5A-5C are drawings depicting perspective views of various distal ends of the stylet that may be produced by the steps of FIGS. 4A and 4 B.
Figure 5B:
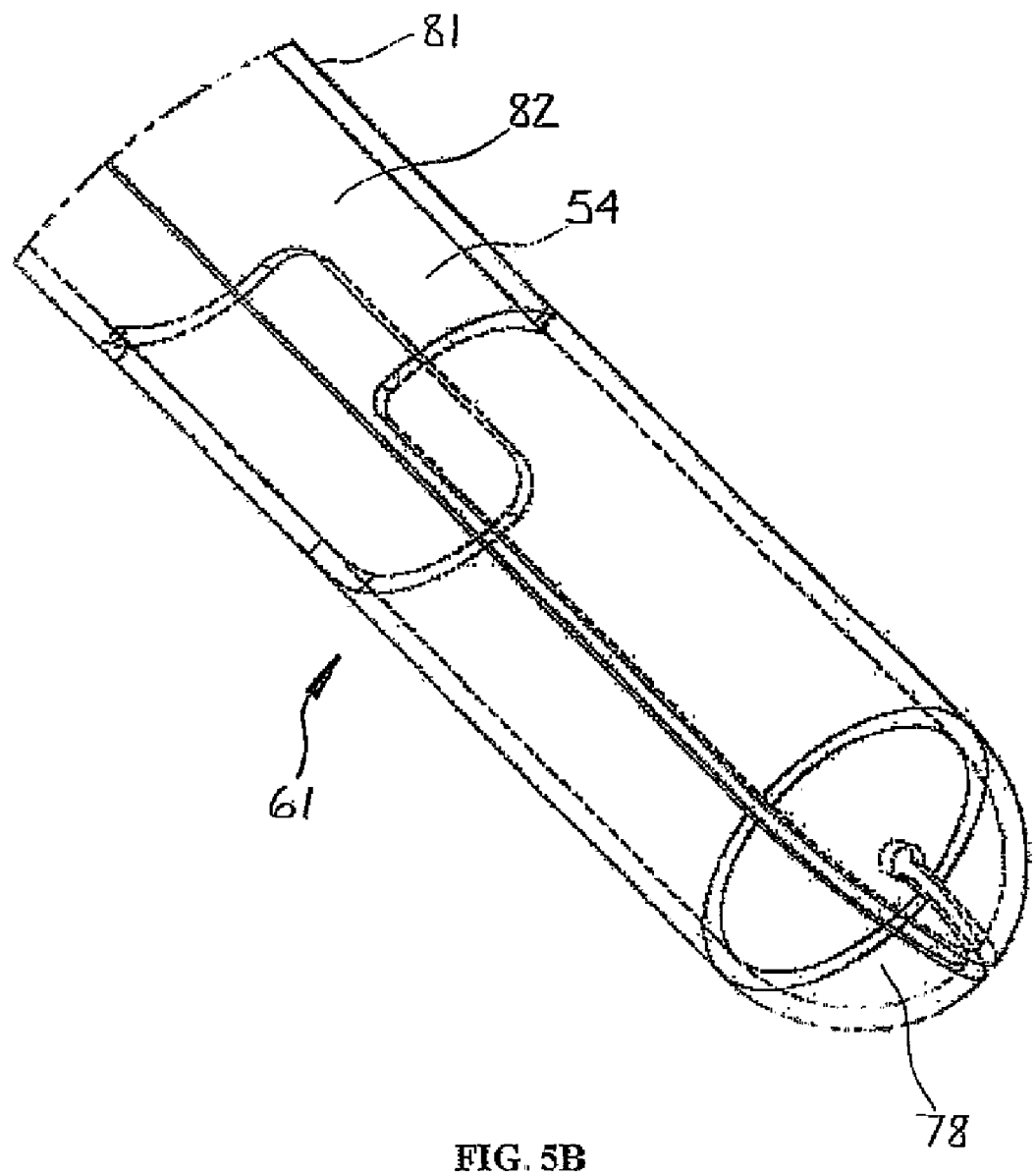
Figure 5C:
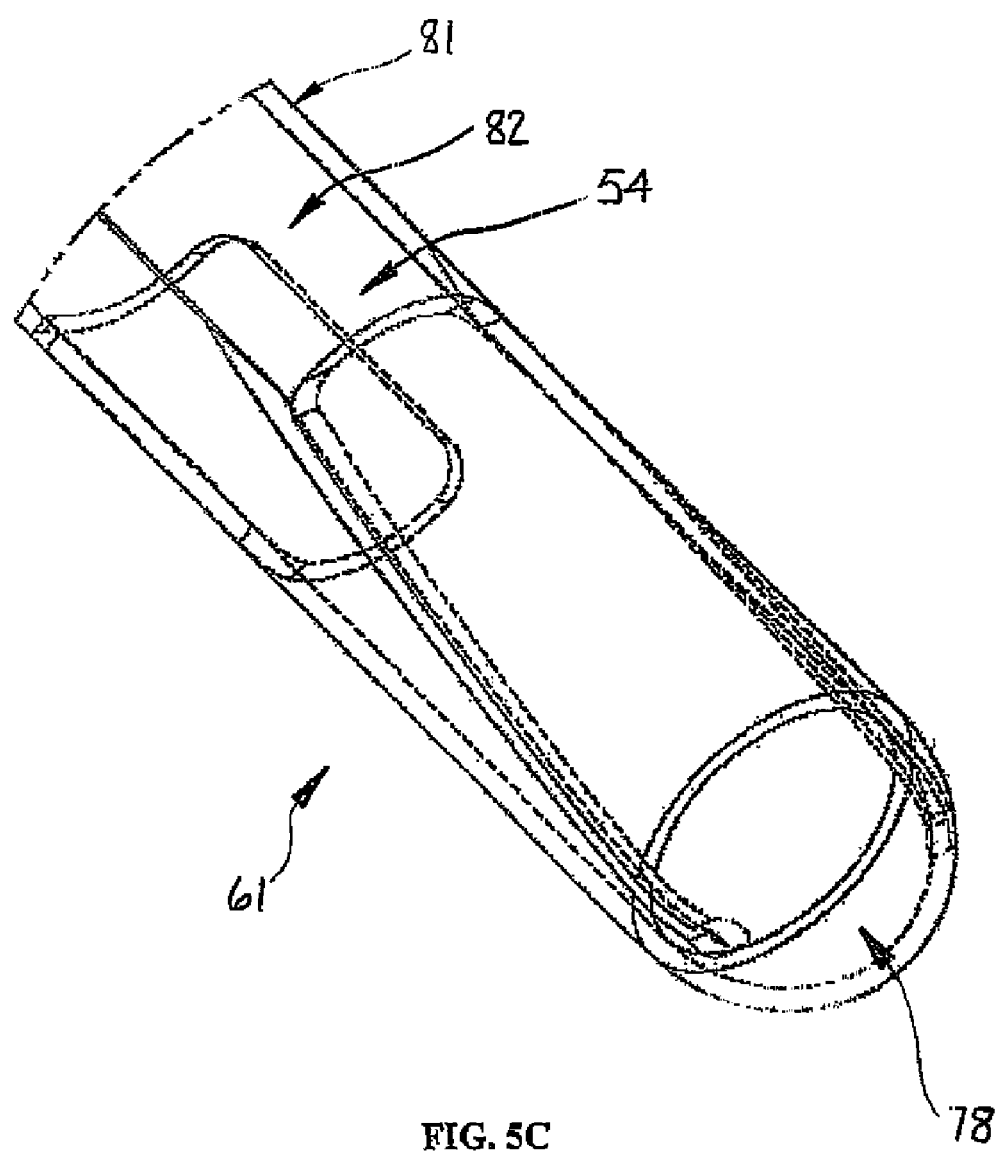

There are many variations on the foregoing concept, many of which are described in U.S. Pat. No. 6,656,160. Others are shown in FIGS. 5A-C. For example, it will be noted that any reduction in the mass of the obturator 61 will result in an increased speed of movement from its initial proximal position to its safe distal position. If this mass is removed from the interior surface of the tube, there will also be an increase in the cross-sectional area of the insufflation channel 54. If an entire section of the wall 81 is removed, the insufflation channel 54 is expanded to include an area up to the internal surface of the wall 34 of the needle 30. By increasing the cross-sectional area of this channel 54, insufflation times associated with the initial inflation of the abdominal cavity can be significantly decreased resulting in a reduction in the time as well as the cost of the procedure. A higher gas insufflation rate also increases the response time of the insufflation apparatus as the gas pressure is maintained throughout the operative procedure.

In order to produce obturators or stylets as described above, metal tubes have been machined to produce the desired three-dimensional configuration, a costly and time-consuming procedure. Described herein is a method of manufacturing the stylets using a more cost-effective and efficient technique, using a thin sheet of metal in a progressive die to stamp and roll the metal into the final configuration.

In the present invention, a thin sheet of metal 100 is subjected to a series of progressive steps, including, potentially, stamping, punching, coining, bending, deep drawing, wire-forming, fine blanking, multislide stamping and fourslide stamping. An automated feeding system pushes the thin metal sheet, in some cases unrolling it from a coil, through various stations at which various operations are performed until the finished stylet has the desired final form. Typically, the final step in the process is a trimming operation, or cut-off operation, which separates the finished stylet from the carrying material, or a clean-up step for removing excess edge material.

In one embodiment, the progressive stamping machine uses a cylindrical type feed cylinder that includes the stamping form or die In other embodiments, the progressive stamping machine uses a reciprocating motion to manufacture the stylet. In this embodiment, the progressive stamping die is placed into a reciprocating stamping press. As the stamping press moves up, the progressive stamping die opens. When the stamping press moves down, the progressive stamping die closes. When the stamping press opens, the metal material is able to feed. As the stamping press closes, the progressive stamping die performs work on the raw material. When the lead part is completed, each stroke of the press results in a completed part being removed from the die.

Metals suitable for use in manufacturing stylets using this technique include any biocompatible metal that may be used in the progressive stamping process. Metals suitable for use in the progressive stamping process include stainless steel, aluminum, brass, cold rolled steel, copper, galvanized steel, hot rolled steel, titanium and zinc. Preferably, stainless steel is used to manufacture the stylet.

Figure 3:
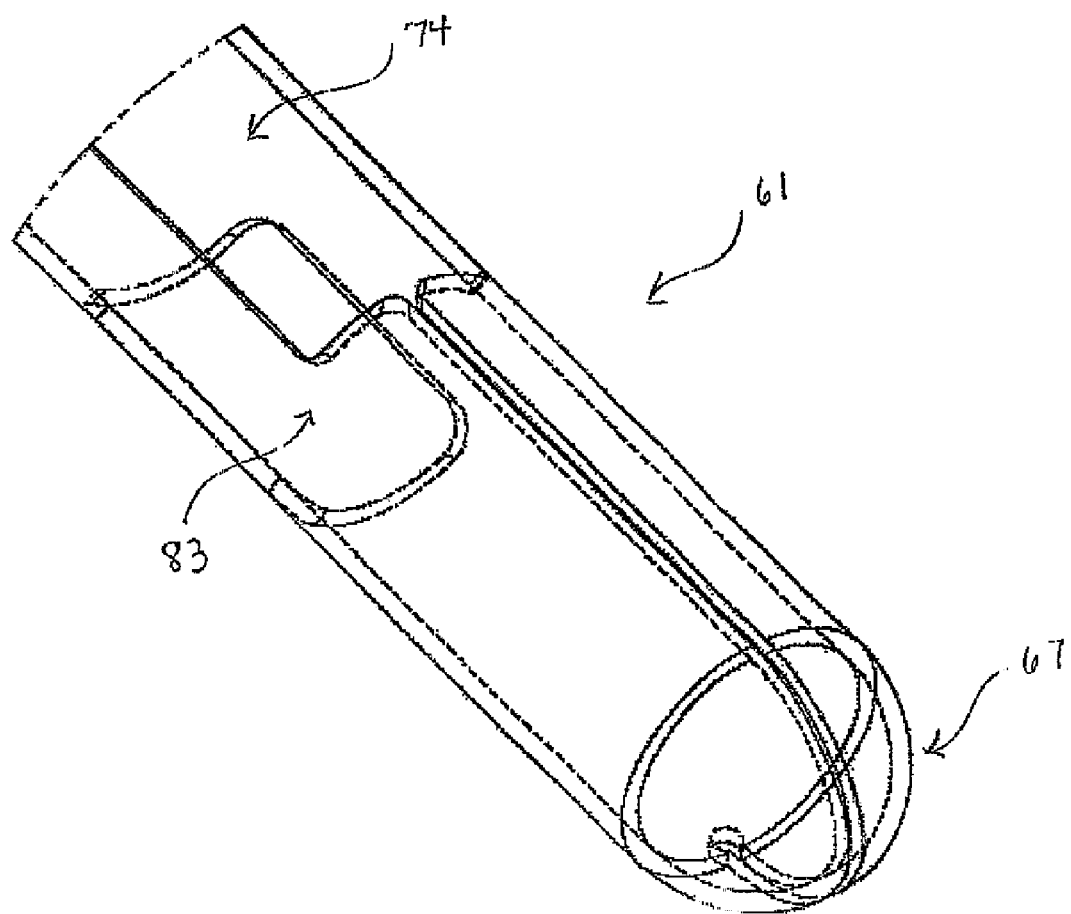
FIG. 3 is a drawing showing a close-up of the distal end of the stylet shown in FIG. 2.

Referring to FIGS. 4A and 4B, a process of the present invention, used to create a stylet 61 as shown in FIGS. 2 and 3, is depicted. FIG. 4A shows a top-down view of a thin metal sheet 100 and a series of steps that may be used to produce the final stylet 61. FIG. 4B shows a side view of the metal sheet 100, between punches 150 that may be used to produce the final configuration of the sheet.

Briefly, a thin metal sheet 100 may be moved through a progressive die, and a series of stamps, punches, and rollers may be used to produce the final stylet. In this example, the progressive steps are shown as steps 101-124 in FIG. 4A. After each step, the sheet 100 is advanced to the next station for the next step. A set of particular steps used to create a stylet 61 of FIGS. 2 and 3 is shown in Table 1.

TABLE 1

| | |
|---|---|
| 101 | Link point score marking and square hole piercing |
| 102 | Pilot hole piercing |
| 103 | Profile notching |
| 104 | Idle |
| 105 | Profile notching |
| 106 | Idle |
| 107 | Profile notching |
| 108 | Link point lancing down |
| 109 | Form up |
| 110 | Idle |
| 111 | Idle |
| 112 | Idle |
| 113 | Form up |
| 114 | Link point lance down |
| 115 | Scrap cut-down |
| 116 | Idle |
| 117 | Form up |
| 118 | Idle |
| 119 | Rounding form |
| 120 | Idle |
| 121 | Sizing |
| 122 | Idle |
| 123 | Scrap cut-down |
| 124 | Parting off and blow out |

Referring to FIGS. 4A and 4B, the method for forming the stylet 61 includes providing a flat sheet of metal 100 and forming pilot holes 152 in the sheet of metal proximate opposed edges 154 of the sheet of metal. A strip 156 having a configuration of a flat pattern of the stylet 61 is formed within the sheet 100 and remains affixed to the sheet during forming of the stylet by at least one support tab 158. The strip 156, or flat pattern, is progressively formed into a stylet 61. When formation of the stylet 61 is complete, the stylet is trimmed from the sheet 100 by cutting the at least one support tab 158. The strip 156 may be formed by forming openings 160 along each side of the strip that correspond with the length of the flat pattern of the stylet 61. The openings 160 are separated by a distance that corresponds to a width of the strip 156. The profile of the edges 162 along the length of the flat pattern of the stylet 61 is included along the edges of the openings 160 closest to each other. The at least one support tab 158 may include a first support tab 164 that is positioned between the proximal end 166 of the strip 156 and the sheet of metal 100 and at least one second support tab 168 positioned between each side 162 of the strip and the sheet of metal. As can be seen in FIGS. 4A and 4B, multiple stylets 61 may be sequentially formed from the sheet of metal 100.

The advantages of stylets made according to the process described herein include allowance for a high insufflation rate while reducing component cost. The high insufflation flow rate is achieved by removing a portion of the stylet circumference over the majority of the length. This increases cross-sectional area and allows for higher flow through the needle. The tip portion is still completely cylindrical and maintains a blunt tip. There are openings behind the blunt tip which are equal to or greater than the cross-sectional area of the inner portion of the needle with the stylet in place. These openings allow gas to flow into the abdomen after the needle as been inserted. The low cost is achieved by forming the entire part out of a thin piece of sheet metal rather than machining and forming the stylet from a drawn thin walled tube, as was previously done.

Many alterations and modifications may be made by those having ordinary skill in the art without departing from the spirit and scope of the invention. For these reasons, the above description should not be construed as limiting the invention, but should be interpreted as merely exemplary of aspects thereof.

The invention claimed is:

1. A method for forming a high flow insufflation needle stylet, comprising:
   providing a flat sheet of metal;
   forming pilot holes in the sheet of metal proximate opposed edges of the sheet of metal;
   forming a strip within the sheet, the strip remaining affixed to the sheet at all times during forming by at least one support tab, the strip being in the configuration of a flat pattern of the stylet;
   progressively forming the strip into a stylet having a distal section, an intermediate section and a proximal section extending proximally of the intermediate section, the distal section being formed into a substantially cylindrical shape having a closed distal end, the intermediate section and the proximal section being formed into a partial cylindrical shape with edges of the strip in the intermediate section and the proximal section being formed to between about 90° and 180° apart with the proximal section having an open proximal end; and
   trimming the stylet from the sheet by cutting the at least one support tab.

2. The method of claim 1, wherein:
   the forming a strip step including forming openings along each side of the strip, the openings corresponding with the length of the flat pattern of the stylet, the openings being separated by a distance corresponding to a width of the strip.

3. The method of claim 2, edges of the openings closest to each other comprising a profile of the edges along the length of the flat pattern of the stylet.

4. The method of claim 2, the at least one support tab including a first support tab positioned between the proximal end of the strip and the sheet of metal and at least one second support tab positioned between each side of the strip and the sheet of metal.

5. The method of claim 1, the closed distal end of the stylet being formed into a semispherical shape.

6. The method of claim 1, further comprising sequentially forming multiple stylets from the sheet of metal.

7. The method of claim 1, further comprising forming apertures in the strip.

8. The method of claim 1 wherein the step of forming a strip within the sheet includes forming the flat pattern of the stylet that includes first and second side edges extending along the length of the pattern, a distal section, an intermediate section and a proximal section extending proximally of the intermediate section; and
   wherein the step of progressively forming the strip into a stylet includes approximating the first side edges of the distal section to the second side edges of the distal section.

9. The method of claim 8 wherein the distal end
   wherein the step of progressively forming the strip into a stylet includes forming at least a portion of the distal section into a cylindrical shape with substantially the same diameter as the partial cylindrical shape of the intermediate section.

10. The method of claim 8 further including the step of forming an outlet port in the distal section of the flat pattern of the stylet.

11. The method of claim 8 wherein the step of forming the strip into a stylet includes forming an opening along the first and second side edges extending from the proximal end to the distal end along the entire length of the stylet.

12. The method of claim 11 wherein the opening along the first and second side edges is narrower at the distal section relative to the intermediate section.

13. The method of claim 8 wherein the step of forming a strip within the sheet includes forming the strip such that the distal section of the flat pattern of the stylet is wider than the intermediate section.

14. A method for forming a high flow insufflation needle stylet, the stylet having a distal section, an intermediate section and a proximal section extending proximally of the intermediate section, comprising:
   providing a flat sheet of metal;
   forming pilot holes in the sheet of metal proximate opposed edges of the sheet of metal;
   forming a profile of a flat pattern of the stylet within the sheet with at least one support tab positioned between the flat pattern of the stylet and the sheet, the flat pattern having a proximal end, a distal end and a pair of substantially longitudinal edges;
   progressively forming the intermediate section of the stylet and the proximal section of the stylet into a partial cylindrical shape with the proximal end being open and the longitudinal edges in the intermediate section and the proximal section being positioned between about 90° and 180° apart;
   progressively forming the distal section into a substantially cylindrical shape having a closed distal end; and
   trimming the stylet from the sheet by cutting the at least one support tab.

15. The method of claim 14, the at least one support tab including a first support tab positioned between the proximal end of the flat pattern of the stylet and the sheet of metal and at least one second support tab positioned between each side of the flat pattern of the stylet and the sheet of metal.

16. The method of claim 14, the closed distal end of the stylet being formed into a semispherical shape.

17. The method of claim 14, further comprising sequentially forming multiple stylets from the sheet of metal.

18. The method of claim 14, further comprising forming apertures in the flat pattern of the stylet.

* * * * *